(12) United States Patent
Kotov et al.

(10) Patent No.: US 11,313,001 B2
(45) Date of Patent: Apr. 26, 2022

(54) COMPOSITIONS AND METHODS FOR DETECTION OF MICROORGANISMS

(71) Applicant: THE REGENTS OF THE UNIVERSITY OF MICHIGAN, Ann Arbor, MI (US)

(72) Inventors: Nicholas Kotov, Ann Arbor, MI (US); Jeremy Scott VanEpps, Ann Arbor, MI (US); Kevin Ward, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 80 days.

(21) Appl. No.: 16/761,686

(22) PCT Filed: Nov. 6, 2018

(86) PCT No.: PCT/US2018/059387
§ 371 (c)(1),
(2) Date: May 5, 2020

(87) PCT Pub. No.: WO2019/090306
PCT Pub. Date: May 9, 2019

(65) Prior Publication Data
US 2021/0180117 A1    Jun. 17, 2021

Related U.S. Application Data
(60) Provisional application No. 62/581,950, filed on Nov. 6, 2017.

(51) Int. Cl.
*C12Q 1/689* (2018.01)
*C12Q 1/686* (2018.01)

(52) U.S. Cl.
CPC ............ *C12Q 1/689* (2013.01); *C12Q 1/686* (2013.01)

(58) Field of Classification Search
CPC ................................. C12Q 1/689; C12Q 1/686
See application file for complete search history.

(56) References Cited

U.S. PATENT DOCUMENTS

| | | | |
|---|---|---|---|
| 2003/0143604 A1 | 7/2003 | Storhoff et al. | |
| 2009/0286286 A1 | 11/2009 | Lim et al. | |
| 2012/0164644 A1* | 6/2012 | Neely | C12Q 1/6816 435/6.11 |
| 2013/0123480 A1 | 5/2013 | Todd et al. | |
| 2016/0355871 A1* | 12/2016 | Want | C12Q 1/689 |

OTHER PUBLICATIONS

Ma et al., Nature Communications, 4:2689, pp. 1-8, (Year: 2013).*
Ma. W., et al. Attomolar DNA detection with chiral nanorod assemblies. Nat Commun. 2013;4:2689.
Alsara, O., et al. Advanced age and the clinical outcomes of transcatheter aortic valve implantation. J Geriatr Cardiol. Jun. 2014;11(2):163-70.
Bryers, J. D. Medical biofilms. Biotechnol Bioeng. May 1, 2008;100(1):1-18.
Cleven, B. E. E. et al. Identification and characterization of bacterial pathogens causing bloodstream infections by DNA microarray. J Clin Microbiol. Jul. 2006;44(7):2389-97.
Darouiche, R. O., Treatment of infections associated with surgical implants. N Engl J Med. Apr. 1, 2004;350(14):1422-9.
Greenspon, A. J. et al. 16-year trends in the infection burden for pacemakers and implantable cardioverter-defibrillators in the United States 1993 to 2008. J Am Coll Cardiol. Aug. 30, 2011;58(10):1001-6.
Habib, G. et al. 2015 ESC Guidelines for the management of infective endocarditis: The Task Force for the Management of Infective Endocarditis of the European Society of Cardiology (ESC). Endorsed by: European Association for Cardio-Thoracic Surgery (EACTS), the European Association of Nuclear Medicine (EANM). Eur Heart J. Nov. 21, 2015;36(44):3075-3128.
Hall, K. K. et al. Updated review of blood culture contamination. Clin Microbiol Rev. Oct. 2006;19(4):788-802.
Hall-Stoodley, L. et al. Towards diagnostic guidelines for biofilm-associated infections. FEMS Immunol Med Microbiol. Jul. 2012;65(2):127-45.
Isaacs, A. J., et al. National trends in utilization and in-hospital outcomes of mechanical versus bioprosthetic aortic valve replacements. J Thorac Cardiovasc Surg. May 2015;149(5):1262-9.e3.
Kermekchiev, M. B., et al. Mutants of Taq DNA polymerase resistant to PCR inhibitors allow DNA amplification from whole blood and crude soil samples. Nucleic Acids Res. Apr. 2009;37(5):e40.
Khan, W., et al. Implantable medical devices. Focal Controlled Drug Delivery (eds Abraham J. Domb & Wahid Khan) 33-59 (Springer US, 2014).
Lindsay, D. et al. Bacterial biofilms within the clinical setting: what healthcare professionals should know. J Hosp Infect. Dec. 2006;64(4):313-25.
Ma, W. et al. The neurotoxic effect of astrocytes activated with toll-like receptor ligands. J Neuroimmunol. Jan. 15, 2013;254(1-2):10-8.
Mozaffarian, D. et al. Heart Disease and Stroke Statistics—2016 Update. A Report From the American Heart Association, doi:10.1161/cir.0000000000000350 (2015)).
Neut, D., et al. The role of small-colony variants in failure to diagnose and treat biofilm infections in orthopedics. Acta Orthop. Jun. 2007;78(3):299-308.
Nielsen, J. C., et al., Infected cardiac-implantable electronic devices: prevention, diagnosis, and treatment. Eur Heart J. Oct. 1, 2015;36(37):2484-90.
Peters, R. P. H., et al. New developments in the diagnosis of bloodstream infections. Lancet Infect Dis. Dec. 2004;4(12):751-60.

(Continued)

*Primary Examiner* — Cynthia B Wilder
(74) *Attorney, Agent, or Firm* — Casimir Jones, S.C.; Tanya A. Arenson

(57) ABSTRACT

Provided herein are compositions, systems, and methods for detecting microorganisms. In particular, provided herein are compositions, systems, and methods for rapid, multiplex detection of microorganism in unpurified biological samples.

13 Claims, 6 Drawing Sheets

Specification includes a Sequence Listing.

(56) References Cited

Praz, F., et al. Expanding Indications of Transcatheter Heart Valve Interventions. JACC Cardiovasc Interv. Dec. 21, 2015;8(14):1777-96.

Sango, A. et al. Stewardship approach for optimizing antimicrobial therapy through use of a rapid microarray assay on blood cultures positive for *Enterococcus* species. J Clin Microbiol. Dec. 2013;51(12):4008-11.

Valencia-Shelton, F. et al. Nonculture techniques for the detection of bacteremia and fungemia. Future Microbiol. 2014;9(4):543-59.

Wang, A. et al. Contemporary clinical profile and outcome of prosthetic valve endocarditis. JAMA. Mar. 28, 2007;297(12):1354-61.

Weinstein, M. P. Blood culture contamination: persisting problems and partial progress. J Clin Microbiol. Jun. 2003;41(6):2275-8.

Yanagihara, K. et al. Evaluation of pathogen detection from clinical samples by real-time polymerase chain reaction using a sepsis pathogen DNA detection kit. Crit Care. 2010;14(4):R159.

Zhan, C., et al. Cardiac device implantation in the United States from 1997 through 2004: a population-based analysis. J Gen Intern Med. Jan. 2008;23 Suppl 1 (Suppl 1):13-9.

Zhao, Y. et al. Shell-engineered chiroplasmonic assemblies of nanoparticles for zeptomolar DNA detection. Nano Lett. Jul. 9, 2014;14(7):3908-13.

* cited by examiner

SEQUENCE LISTING

<160> NUMBER OF SEQ ID NOS: 14

<210> SEQ ID NO 1
<211> LENGTH: 20
<212> TYPE: DNA
<213> ORGANISM: Artificial sequence
<220> FEATURE:
<223> OTHER INFORMATION: Synthetic

<400> SEQUENCE: 1
agagtttgat cctggctcag                                            20

<210> SEQ ID NO 2
<211> LENGTH: 19
<212> TYPE: DNA
<213> ORGANISM: Artificial sequence
<220> FEATURE:
<223> OTHER INFORMATION: Synthetic

<400> SEQUENCE: 2
gtattaccgc ggctgctgg                                             19

<210> SEQ ID NO 3
<211> LENGTH: 20
<212> TYPE: DNA
<213> ORGANISM: Artificial squence
<220> FEATURE:
<223> OTHER INFORMATION: Synthetic

<400> SEQUENCE: 3
aactgttggc cactatgagt                                            20

<210> SEQ ID NO 4
<211> LENGTH: 21
<212> TYPE: DNA
<213> ORGANISM: Artificial sequence
<220> FEATURE:
<223> OTHER INFORMATION: Synthetic

<400> SEQUENCE: 4
ccagcattac ctgtaatctc g                                          21

<210> SEQ ID NO 5
<211> LENGTH: 26
<212> TYPE: DNA
<213> ORGANISM: Artificial sequence
<220> FEATURE:
<223> OTHER INFORMATION: Synthetic

<400> SEQUENCE: 5
aagcgacttc acatctatta ggttat                                     26

<210> SEQ ID NO 6
<211> LENGTH: 26
<212> TYPE: DNA
<213> ORGANISM: Artificial sequence
<220> FEATURE:
<223> OTHER INFORMATION: Synthetic

<400> SEQUENCE: 6
tatattcttc gttactcatg ccatac                                     26

<210> SEQ ID NO 7
<211> LENGTH: 22
<212> TYPE: DNA
<213> ORGANISM: Artificial sequence

```
<220> FEATURE:
<223> OTHER INFORMATION: Synthetic

<400> SEQUENCE: 7
cattgatcgc aacgttcaat tt                                    22

<210> SEQ ID NO 8
<211> LENGTH: 21
<212> TYPE: DNA
<213> ORGANISM: Artificial sequence
<220> FEATURE:
<223> OTHER INFORMATION: Synthetic

<400> SEQUENCE: 8
tggtctttct gcattcctgg a                                     21

<210> SEQ ID NO 9
<211> LENGTH: 20
<212> TYPE: DNA
<213> ORGANISM: Artificial sequence
<220> FEATURE:
<223> OTHER INFORMATION: Synthetic

<400> SEQUENCE: 9
ccaccctcaa acaggtgaat                                       20

<210> SEQ ID NO 10
<211> LENGTH: 20
<212> TYPE: DNA
<213> ORGANISM: Artificial sequence
<220> FEATURE:
<223> OTHER INFORMATION: Synthetic

<400> SEQUENCE: 10
aacgttgtaa ccaccccaag                                       20

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
gcagacaaat tgggtggttt                                       20

<210> SEQ ID NO 12
<211> LENGTH: 20
<212> TYPE: DNA
<213> ORGANISM: Artificial sequence
<220> FEATURE:
<223> OTHER INFORMATION: Synthetic

<400> SEQUENCE: 12
catcgttacg gattgcttca                                       20

<210> SEQ ID NO 13
<211> LENGTH: 26
<212> TYPE: DNA
<213> ORGANISM: Artificial sequence
<220> FEATURE:
<223> OTHER INFORMATION: Synthetic

<400> SEQUENCE: 13
aagcgacttc acatctatta ggttat                                26
```

```
<210> SEQ ID NO 14
<211> LENGTH: 26
<212> TYPE: DNA
<213> ORGANISM: Artificial sequence
<220> FEATURE:
<223> OTHER INFORMATION: Synthetic

<400> SEQUENCE: 14
tatattcttc gttactcatg ccatac                                              26
```

COMPOSITIONS AND METHODS FOR DETECTION OF MICROORGANISMS

CROSS REFERENCE TO RELATED APPLICATION

This application is a 371 U.S. National Phase Entry of pending International Application No. PCT/US2018/059387, filed Nov. 16, 2018, which claims priority to and the benefit of U.S. Provisional Application No. 62/581,950, filed Nov. 6, 2017, each of which is hereby incorporated by reference in its entirety.

FIELD OF DISCLOSURE

Provided herein are compositions, systems, and methods for detecting microorganisms. In particular, provided herein are compositions, systems, and methods for rapid, multiplex detection of microorganism in unpurified or complex biological samples.

BACKGROUND

Bioengineering advances in electronics and materials have produced an astonishing array of medical devices implanted directly in the bloodstream, including prosthetic heart valves, pacemakers, defibrillators, ventricular assist devices, dialysis catheters, venous filters, and stents. These innovations have prolonged and improved the quality of lives of millions of patients. Unfortunately, the presence of a foreign material within the bloodstream provides a niche for bacterial colonization and infection. Over 1.2 million healthcare-associated infections can be attributed to indwelling medical devices (Bryers, J. D. Biotechnology and Bioengineering 100, 1-18, doi:10.1002/bit.21838 (2008); Darouiche, R. O. TN Engl J Med 350, 1422-1429, doi: 10.1056/NEJMra035415350/14/1422 [pii] (2004)).

Intravascular devices are becoming one of the leading causes of bloodstream infection in U.S. This is exemplified by the fact that increases in infection rates for cardiac electrical implanted devices have outpaced increases in implantation rates (Nielsen, J. C., et al., European heart journal, doi:10.1093/eurheartj/ehv060 (2015); Greenspon, A. J. et al. Journal of the American College of Cardiology 58, 1001-1006, doi:10.1016/j.jacc.2011.04.033 (2011)). As technologies such as transcatheter aortic valve replacement and expanding indications allow patients with increasing comorbidities to receive intravascular implants, this trend will continue or get worse in the short term. While new antimicrobial technologies are emerging, the time horizon for their development and approval is quite long.

A major obstacle associated with intravascular device related infection is establishing the diagnosis. There are no established biomarkers for detection of bacterial colonization or bacteremia. Currently blood cultures are used to detect and identify pathogens. This is not optimal for the following reasons: Cultures have low sensitivity; up to 30% of prosthetic valve endocarditis is culture negative (Habib, G. et al. 2015 European heart journal 36, 3075-3128, doi: 10.1093/eurheartj/ehv319 (2015)). The time to result for blood cultures ranges from 24-72 hours. Worse still, cultures lack specificity and are routinely contaminated with normal skin flora (Hall, K. K. & Lyman, J. A. Clinical Microbiology Reviews 19, 788-802, doi:10.1128/cmr.00062-05 (2006)). Understanding that early antimicrobial therapy reduces mortality in bloodstream infections, patients are given empiric broad-spectrum antibiotics pending the results of this poor diagnostic. The result is a one size fits all use of antibacterial drugs which leads to antibiotic resistance, opportunistic infection (e.g., *Clostridium difficile*), severe side effects (e.g., renal or hepatic failure), or under treatment of critically ill patients.

Technologies that aide in the early diagnosis of intravascular implant infections are needed to reduce morbidity and mortality in patients using such devices.

SUMMARY

Provided herein are compositions, systems, and methods for detecting microorganisms. In particular, provided herein are compositions, systems, and methods for rapid, multiplex detection of microorganism in unpurified or biological samples, such as blood.

For example, in some embodiments, provided herein is a method of detecting a plurality of microorganisms in a biological sample, comprising: a) performing nucleic acid amplification (e.g., PCR) on a biological sample (e.g., with a plurality of forward and reverse primers, wherein the primers are attached to a nanoparticle) to generate a plurality of amplification products of different lengths comprising nanoparticles; b) depositing a metal shell on the nanoparticles incorporated in the amplification products to generate amplification products comprising metal coated nanoparticles; and c) detecting the amplification products comprising metal coated nanoparticles using circular dichroism (CD). In some embodiments, the nanoparticles are gold nanoparticles. In some embodiments, the forward and said reverse primers comprise nanoparticles of different sizes. In some embodiments, the nanoparticles are nanorods. In some embodiments, the amplification products comprising metal nanoparticles assemble into side by side ladders comprising gap distance between nanoparticles. In some embodiments, the amplification products of different lengths exhibit CD peaks of different wavelengths. In some embodiments, the metal shell is gold, copper, or silver. In some embodiments, the microorganisms are bacteria. In some embodiments, the bacteria are pathogenic bacteria (e.g., antibiotic resistant bacteria). In some embodiments, the primers amplify a plurality of organism-specific and/or antibiotic resistance genes. In some embodiments, the said biological sample is whole blood. In some embodiments, the sample is not cultured or purified prior to performing the method. In some embodiments, the method is performed in 3 hours or less (e.g., 2.9, 2.8, 2.7, 2.6, 2.5, or less). In some embodiments, the method further comprises the step of contacting the sample with an antibiotic prior to performing the method.

Further embodiments provide a method of detecting a plurality of microorganisms in a biological sample, comprising: a) contacting a biological sample comprising a pathogenic bacteria with an antibiotic; b) performing amplification (e.g., PCR) on the biological sample (e.g., with a plurality of forward and reverse primers, wherein the primers are attached to a nanoparticle) to generate a plurality of amplification products of different lengths comprising nanoparticles; c) depositing a metal shell on the nanoparticles incorporated in said amplification products to generate amplification products comprising metal coated nanoparticles; and d) detecting the amplification products comprising metal coated nanoparticles using circular dichroism (CD).

Yet other embodiments provide composition or kit, comprising at least one pair of amplification primers comprising a plurality of forward and reverse primers, wherein the primers are attached to a nanoparticle. In some embodiments, the composition or kit further comprises one or more components selected, for example, a metal, an antibiotic, a control nucleic acid, one or more buffers, and one or more enzymes.

Still other embodiments provide a reaction mixture, comprising: a plurality of forward and reverse primers, wherein the primers are attached to a nanoparticle bound to a target nucleic acid or an amplification product thereof. In some embodiments, the reaction mixture is coated with a metal.

Additional embodiments are described herein.

DEFINITIONS

Figure 1:
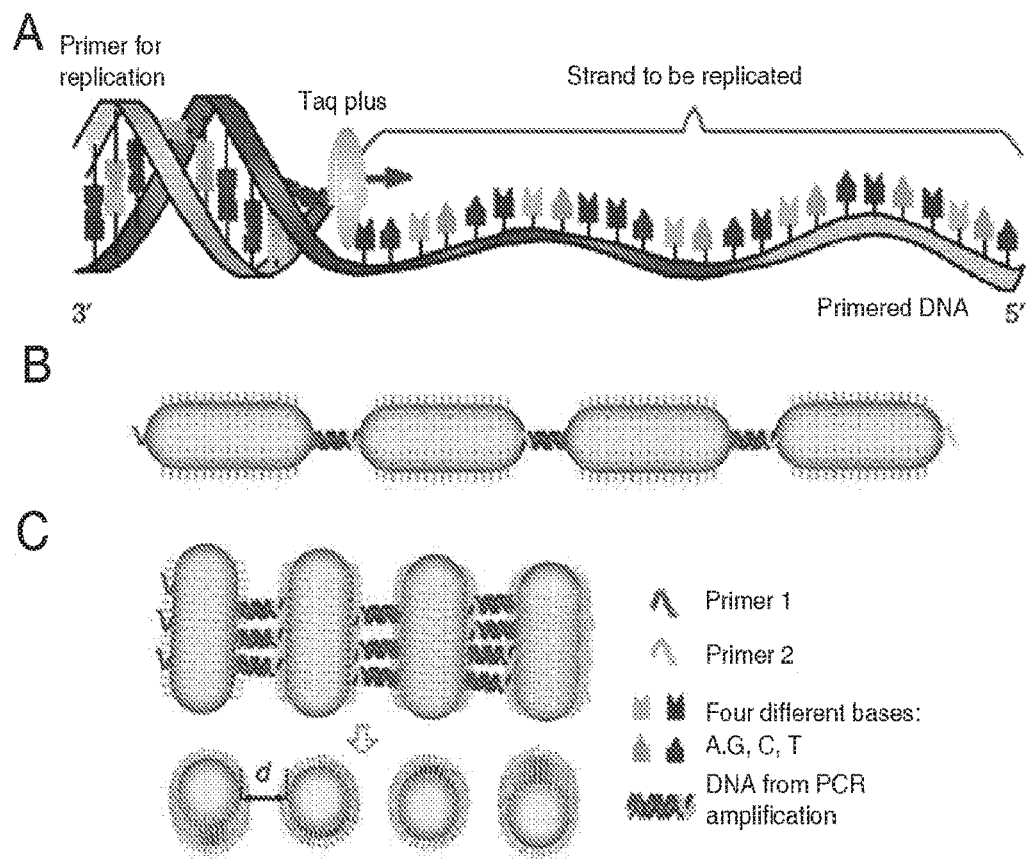
FIG. 1 shows (A) PCR replication procedure in which a DNA strand is amplified using primer, template DNA, taq plus polymerase and four different DNA bases. (B) PCR-based gold nanorods (NRs) end-to-end (ETE) assembly. (C) PCR-based gold NRs side-by-side (SBS) assembly with inter-NR gap d; in the bottom part of the panel the DNA chains were removed for clarity. Representative electron microscopy for ETE (D-F) and SBS (G-I) assemblies obtained after different number of PCR cycles, n=2 (D & G), n=10 (E & H), n=15 (F & I). Cry electron tomography for SBS assembly (J) and CD spectra.
Figure 1:
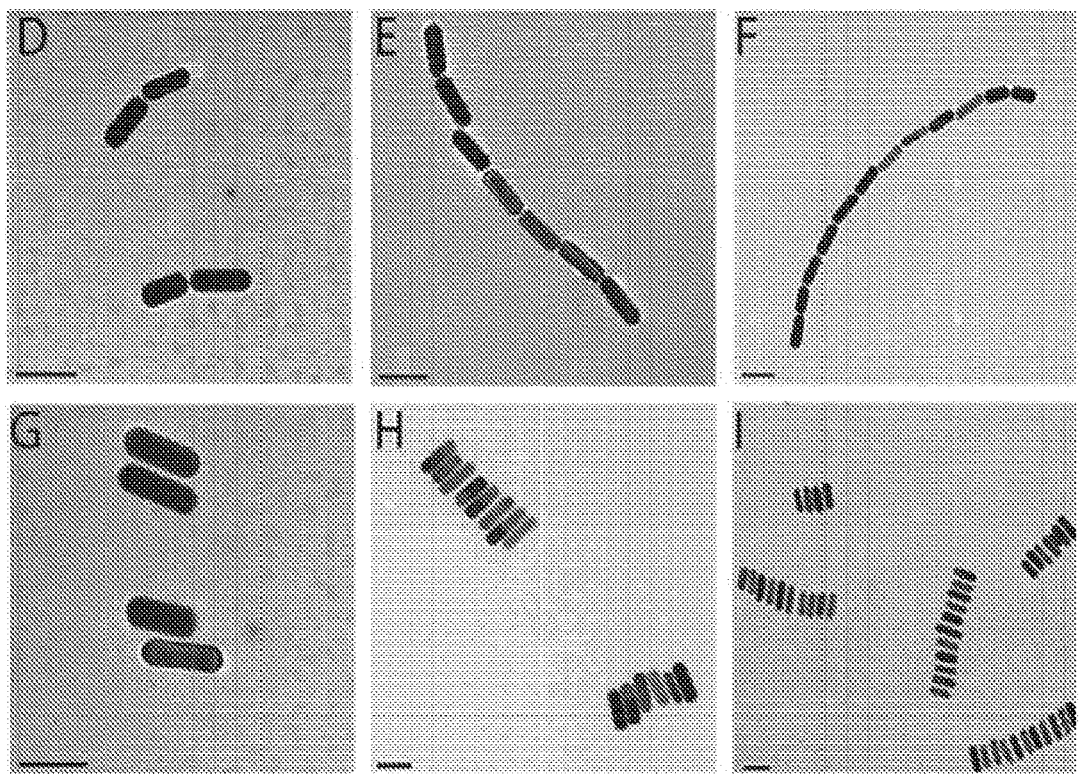
Figure 1:
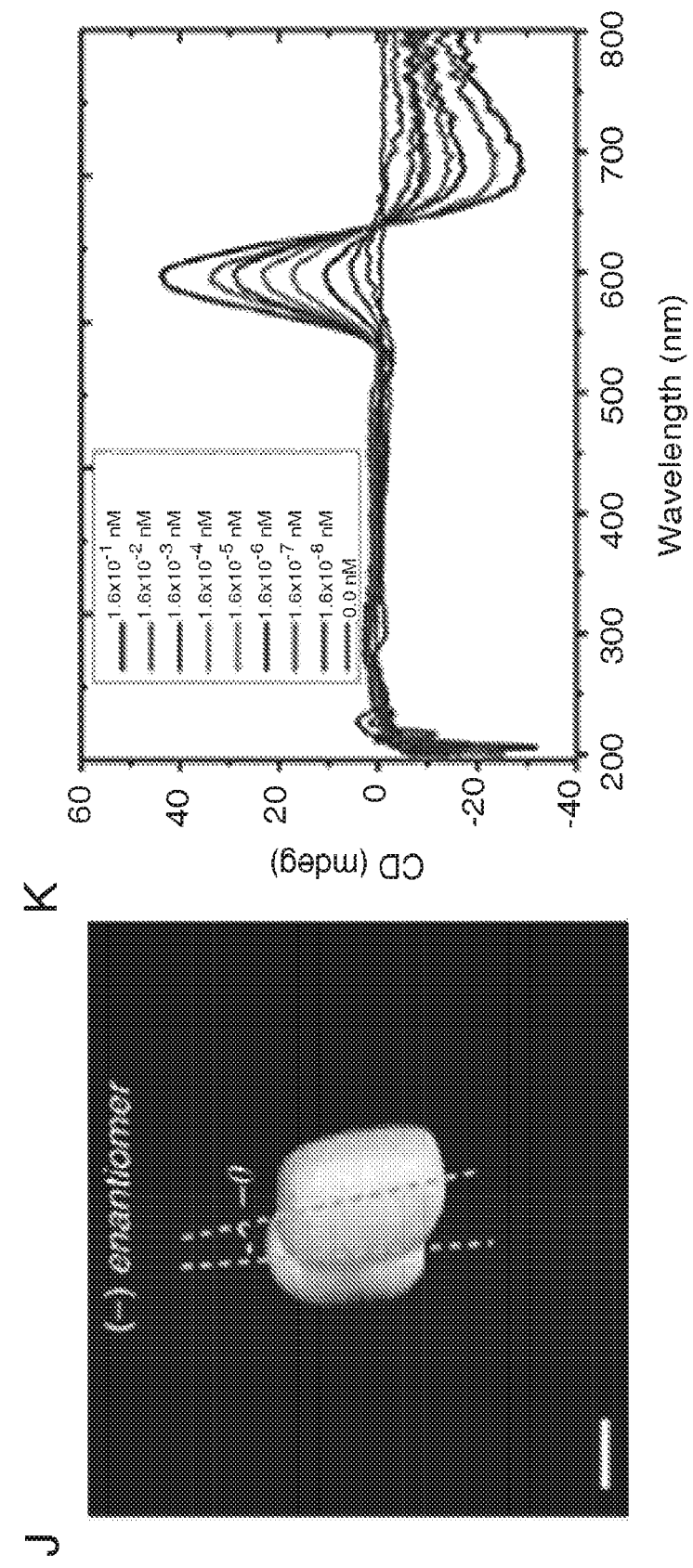

To facilitate an understanding of the present technology, a number of terms and phrases are defined below. Additional definitions are set forth throughout the detailed description.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5 (carboxyhydroxyl¬methyl) uracil, 5-fluorouracil, 5 bromouracil, 5-carboxymethylaminomethyl 2 thiouracil, 5 carboxymethyl¬aminomethyluracil, dihydrouracil, inosine, N6 isopentenyladenine, 1 methyladenine, 1-methylpseudo¬uracil, 1 methylguanine, 1 methylinosine, 2,2-dimethyl¬guanine, 2 methyladenine, 2 methylguanine, 3-methyl¬cytosine, 5 methylcytosine, N6 methyladenine, 7 methylguanine, 5 methylaminomethyluracil, 5-methoxy¬amino¬methyl 2 thiouracil, beta D mannosylqueosine, 5' methoxycarbonylmethyluracil, 5 methoxyuracil, 2 methylthio N6 isopentenyladenine, uracil 5 oxyacetic acid methylester, uracil 5 oxyacetic acid, oxybutoxosine, pseudouracil, queosine, 2 thiocytosine, 5-methyl-2 thiouracil, 2-thiouracil, 4 thiouracil, 5-methyluracil, N-uracil 5 oxyacetic acid methylester, uracil 5 oxyacetic acid, pseudouracil, queosine, 2-thiocytosine, and 2,6 diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "amplicon" refers to a nucleic acid generated via amplification reaction. The amplicon is typically double stranded DNA; however, it may be RNA and/or DNA:RNA. The amplicon comprises DNA complementary to a sample nucleic acid. In some embodiments, primer pairs are configured to generate amplicons from a sample nucleic acid. As such, the base composition of any given amplicon may include the primer pair, the complement of the primer pair, and the region of a sample nucleic acid that was amplified to generate the amplicon. One skilled in the art understands that the incorporation of the designed primer pair sequences into an amplicon may replace the native sequences at the primer binding site, and complement thereof. In certain embodiments, after amplification of the target region using the primers the resultant amplicons having the primer sequences are used for subsequent analysis. In some embodiments, the amplicon further comprises a length that is compatible with subsequent analysis.

The term "amplifying" or "amplification" in the context of nucleic acids refers to the production of multiple copies of a polynucleotide, or a portion of the polynucleotide, typically starting from a small amount of the polynucleotide (e.g., as few as a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, the terms "subject" and "patient" refer to any animal, such as a dog, a cat, a bird, livestock, and particularly a mammal, and preferably a human.

As used herein, the term "sample" is used in its broadest sense. In one sense, it is meant to include a representative portion or culture obtained from any source, including biological and environmental sources. Biological samples may be obtained from animals (including humans) and encompass fluids, solids, tissues, and gases. Biological samples include blood and blood products, such as plasma, serum, and the like. Such examples are not however to be construed as limiting the sample types applicable to the present disclosure.

DETAILED DESCRIPTION

Although the disclosure herein refers to certain illustrated embodiments, it is to be understood that these embodiments are presented by way of example and not by way of limitation.

Provided herein are compositions, systems, and methods for detecting microorganisms. In particular, provided herein are compositions, systems, and methods for rapid, multiplex detection of microorganism in unpurified biological samples. The cardiovascular devices market, specifically those with direct contact with the bloodstream (e.g., pacemakers, defibrillators, prosthetic heart valves, left ventricular assist devices, stents, vascular access devices, and venous filters), is one of the fastest growing medical device industries. This growth is a function of increasing prevalence of cardiovascular disease (Mozaffarian, D. et al. A Report From the American Heart Association, doi:10.1161/cir.0000000000000350 (2015)), expanding indications for implantation (Praz, F., et al. JACC: Cardiovascular Interventions 8, 1777-1796, doi:10.1016/j.jcin.2015.08.015 (2015); Zhan, C., et al. Journal of General Internal Medicine 23, 13-19, doi:10.1007/s11606-007-0392-0 (2008)), and fundamental bioengineering improvements in materials and electronics (Khan, W., Muntimadugu, E., Jaffe, M. & Domb, A. J. in Focal Controlled Drug Delivery (eds Abraham J. Domb & Wahid Khan) 33-59 (Springer US, 2014)). Despite the significant benefits afforded by these devices, any foreign material placed within the bloodstream poses a significant threat of infection. While implantation rates have increased by as much as 65% over the last few decades (Zhan et al. supra; Isaacs, A. J., et al. The Journal of thoracic and cardiovascular surgery 149, 1262-1269.e1263, doi:10.1016/j.jtcvs.2015.01.052 (2015)), infection rates have increased disproportionately (i.e., >200%) (Nielsen et al., supra; Greenspon et al., supra; Wang, A. et al. Jama 297, 1354-1361, doi:10.1001/jama.297.12.1354 (2007)). As a result, implanted medical devices are a leading cause of bloodstream infection in the United States. As indications for implantation continue to expand (Praz et al., supra; Zhan et al., supra), patients with increasing comorbidities receive these devices. For example, the transcatheter aortic valve replacement procedure allows patients who may not otherwise be good candidates for open surgery receive a valve replacement (Alsara, O., et al. Journal of Geriatric Cardiology: JGC 11, 163-170, doi:10.3969/j.issn.1671-5411.2014.02.004 (2014)). Thus, they are anticipated to have greater comorbidity and immunosuppression, and therefore at greater risk for infection. New antimicrobial device strategies are being investigated, but the time horizon for their development, regulatory approval and clinical adoption is quite long.

A central challenge associated with device related infection is that they are caused by biofilms. Biofilms are sessile communities of bacteria encapsulated in an extracellular matrix. They start as colonization of the abiotic material and can progress to disseminated infection 16. Therefore, in many cases the initial presentation is indolent and typically diagnosis is not made until the infection has disseminated. At this point, the device is coated in a mature biofilm, recalcitrant to antibiotics or host immune response. Ultimately the device must be surgically removed and replaced, followed by long-courses of systemic antibiotics. Therefore, early diagnosis of intravascular device contamination will reduce morbidity and mortality and even salvage precious devices.

The current gold standard for diagnosis of intravascular device related infection requires bacterial detection, identification (ID), and AST via traditional blood cultures. This is a very poor diagnostic with profound clinical implications. First, the time to result for blood cultures typically ranges from 1 to 5 days (Cleven, B. E. E. et al. Journal of clinical microbiology 44, 2389-2397, doi:10.1128/jcm.02291-05 (2006)). Once patients have manifested systemic symptoms, broad-spectrum antibiotics are initiated pending culture results. This empiric use of antibiotics results in opportunistic infections, drug-related toxicities, and antibiotic resistance. Second, blood cultures have low sensitivity. When bacteria in the blood are in low numbers, such as when a device is colonized but prior to dissemination, growth is sufficiently slow to produce a negative result (Neut, D., et al. Acta orthopaedica 78, 299-308, doi:10.1080/17453670710013843 (2007); Hall-Stoodley, L. et al. FEMS immunology and medical microbiology 65, 127-145, doi:10.1111/j.1574-695X.2012.00968.x (2012); Lindsay, D. & von Holy, A. The Journal of hospital infection 64, 313-325, doi:10.1016/j.jhin.2006.06.028 (2006)). Worse still, certain bacteria do not grow at all under standard culture conditions (Peters, R. P. H., et al. The Lancet Infectious Diseases 4, 751-760, doi:dx.doi.org/10.1016/51473-3099(04)01205-8 (2004)). For example, up to 30% of prosthetic valve endocarditis is initially culture negative (Habib, G. et al. European heart journal 36, 3075-3128, doi:10.1093/eurheartj/ehv319 (2015)). Therefore, infection is not detected until the biofilm is mature and less susceptible to antibiotics and host response. Third, cultures are routinely contaminated by normal skin flora (Weinstein, M. P. Journal of clinical microbiology 41, 2275-2278, doi:10.1128/jcm.41.6.2275-2278.2003 (2003)), which can grow rapidly and out-compete certain pathogens in culture media. Repeat cultures to confirm contamination versus infection further extend the time to diagnosis.

A rapid, ultrasensitive, culture-free diagnostic for the detection, ID, and AST for bacteremia is needed. Non-culture molecular diagnostic methods are rapidly being incorporated into standard medical microbiology laboratories. Most techniques are based on nucleic acid detection and/or amplification (e.g., PCR). However, direct detection of bacterial nucleic acid in whole-blood remains a challenge. This is related to the fact that bacterial concentration in the blood can be exceedingly low (e.g., <1 CFU/ml) in a high background concentration of human cells (Valencia-Shelton, F. & Loeffelholz, M. Future microbiology 9, 543-559, doi:10.2217/fmb.14.8 (2014)). To date there are no approved diagnostics for direct detection of bacteria without culture pre-enrichment. Although the current molecular techniques that utilize initial culture enrichment improve the time to AST with demonstrated clinical benefits including length of stay and health cost (Sango, A. et al. Journal of clinical microbiology 51, 4008-4011, doi:10.1128/JCM.01951-13 (2013)), they all suffer the failures of blood cultures previously mentioned. The only viable nucleic acid detection system in whole-blood that does not require culture enrichment is the SeptiFast technology (Roche Diagnostics, Mannheim, Germany). Based on manufacturer's insert, it can identify bacteria in <6 hours. However it does not have comprehensive AST. Furthermore, it can only detect down to ~300 CFU/ml. While this may be useful in patients with severe infection or pre-treatment with antibiotics (Yanagihara, K. et al. Critical Care 14, R159-R159, doi:10.1186/cc9234 (2010)), this is not sensitive enough for the many cases of indolent bacteremia from medical device infection which likely have single-digit CFU/ml concentrations.

Accordingly, provided herein is a detection method that addressed the unmet clinical need for detecting microorganisms (e.g., in whole blood). In some embodiments, by coupling standard PCR primers to nanoparticles (e.g., gold nanorods (NR—PCR)), the PCR reaction described herein generates complex nanorod 'ladders'. These assemblies have unique chiroplasmonic properties, which allow for zeptomolar $10^{-21}$ detection using circular dichroism (CD) spectrophotometry (Ma, W. et al. Nat Commun 4, doi: 10.1038/ncomms3689 (2013); Zhao, Y. et al. Nano Letters, doi:10.1021/nl501166m (2014)). The NR—PCR methods of embodiments of the present disclosure are at least 50× more sensitive than the most sensitive PCR detection systems and can be performed in less than 2.5 hours. While other amplification methods can be used, the description herein is illustrated with PCR.

Preferred NR—PCR methods (1) work on whole-blood without prior culture; (2) are capable of multiplexing sufficiently to detect the majority of pathogens; (3) provide antibiotic susceptibility profiles; and (4) provide a time to result less than 3 hours.

By coupling standard PCR primers to gold nanorods (NR—PCR; FIG. 1A-C) the PCR reaction generates complex nanorod assemblies with lengths that depend on the number of PCR cycles (FIG. 1D-I). The side-by-side (SBS) 'ladders' have unique chiroplasmonic properties (FIG. 1J), which allow for the detection of DNA down to the attomolar $10^{-18}$ range via circular dichroism spectrophotometry (FIG. 1K) (Ma et al., supra). This method is at least 50 times more sensitive than the most sensitive PCR detection techniques and 1000 times more sensitive than most traditional PCR used clinically. In addition, the chiroplasmonic detection is particularly sensitive for large (>2 nm) DNA strands where other PCR detection methods lose sensitivity. Having longer DNA targets increases the assay's specificity.

Employing this highly sensitive and specific PCR technology with primers targeted to identify species specific genes greatly impacts the detection and ID of bacteria in whole-blood. The increased sensitivity detects ultralow concentrations of the most fastidious bacteria. It also allows for DNA detection without prior culture growth enrichment. The high specificity increases the number of gene targets that can be assayed in a multiplex system. It also allows detection of bacterial DNA without the need for sample processing to remove excess human DNA.

In some embodiments, the technique utilizes deposition of metal (e.g., Au, Ag, Cu) around the NP assemblies, post-PCR reaction (FIG. 2A). These shell coatings provide a method to modulate the CD spectral peaks (FIG. 2B) (Zhao et al., supra). In addition, they improved the limit of detection down to the zeptomolar $10^{-21}$ range (near single molecule detection; FIG. 2C) (Zhao et al., supra).

The present disclosure is not limited to particular microorganisms. In some embodiments, bacteria (e.g., pathogenic or antibiotic resistant bacteria) are detected. Examples of pathogenic bacteria include, but are not limited to, methicillin resistant *S. Aureus* (MRSA), *M. tuberculosis* (antibiotic sensitive or resistant), *Streptococcus* sp., *Staphylococcus* sp., *Salmonella* sp., *Listeria* sp., *E. coli, Shigella* sp., *Campylobacter* sp., *Pseudomonas* sp., *Bacillus* sp., *Bartonella* sp., *Bordetella* sp., *Borrelia* sp., *Brucella* sp., *Chlamydia* sp., *Clostridium* sp., *Corynebacterium* sp., *Enterococcus* sp., *Francisella* sp., *Haemophilus* sp., *Helicobacter* sp., *Legionella* sp., *Leptospira* sp., *Mycobacterium* sp., *Mycoplasma* sp., *Rickettsia* sp., *Treponema* sp., *Ureaplasma* sp., *Vibrio* sp., and *Yersinia* sp., and *Neisseria* sp.

In some embodiments, a sample of whole blood or other biological sample from a subject is utilized for analysis with or without further purification. In some embodiments, the subject has an implanted medical device (e.g., including but not limited to, a defibrillator, an artificial bone or joint, a heart pacemaker, cosmetic implants, screws, rods, discs, etc., IUDs, and coronary stents).

In some embodiments, NR—PCR comprises the following steps. In some embodiments, PCR is first performed on the biological sample with a plurality of forward and reverse primers attached to a nanoparticle. In some embodiments, primers for 1 or more (e.g., 2, 3, 4, 5, or more) targets are utilized. In some embodiments, each pair of primers is designed to generate a PCR product of a different length, such that a plurality of PCR products of different lengths comprising nanoparticles are generated.

The present disclosure is not limited to particular micro or nanoparticles. Examples, include, but are not limited to, nanorods. In some embodiments, the nanoparticles or nanorods are gold or other suitable material. In some embodiments, the forward and said reverse primers comprise nanoparticles of different sizes. In some embodiments, the PCR products comprising metal nanoparticles assemble into side by side ladders comprising gap distance between nanoparticles. In some embodiments, it is contemplated that the difference in gap size is responsible for the different CD profiles of different length PCR products.

In some embodiments, following PCR, a metal shell is deposited on the PCR products comprising nanoparticles. In some embodiments, the metal shell is gold, copper, or silver or another metal and may be the same or different than the nanoparticle material.

In some embodiments, following depositions, the metal coated PCR products comprising nanoparticles are detected using circular dichroism (CD). In some embodiments, PCR products of differing lengths exhibit different peak CD shift wavelengths, allowing for multiplexing. Circular dichroism (CD) is dichroism involving circularly polarized light, i.e., the differential absorption of left- and right-handed light. Left-hand circular (LHC) and right-hand circular (RHC)

polarized light represent two possible spin angular momentum states for a photon, and so circular dichroism is also referred to as dichroism for spin angular momentum. It is exhibited in the absorption bands of optically active chiral molecules. CD spectroscopy has a wide range of applications in many different fields. UV CD is used to investigate the secondary structure of proteins. UV/Vis CD is used to investigate charge-transfer transitions. Near-infrared CD is used to investigate geometric and electronic structure by probing metal d→d transitions. Vibrational circular dichroism, which uses light from the infrared energy region, is used for structural studies of small organic molecules, and most recently proteins and DNA. In some embodiments, UV/Vis CD is used to detect NR—PCR products.

In some embodiments, the NR—PCR method, from sample acquisition to data collection and analysis, including CD detection, is completed in 3 hours or less (e.g., 3.0, 2.75, 2.5, 2.25, 2.0 hours or less).

In some embodiments, NR—PCR methods include the step of determining antibiotic resistance status and/or specificity of bacteria (e.g., pathogenic bacteria) in the sample. For example, in some embodiments, the sample is contacted with an antibiotic prior to performing the NR—PCR detection method. In some embodiments, multiple samples are each contacted with a different antibiotic (e.g., of different classes or the same class). In some embodiments, samples are incubated with the antibiotic(s) for a period of several hours. In some embodiments, NR—PCR methods are performed at different time points and the growth of bacteria is determined. By comparing the levels of NR—PCR products detected, which reflect growth of the bacteria, the susceptibility of the sample to each antibiotic is determined. In some embodiments, the genetic profile of the microorganism(s) is determined to reveal antibiotic susceptibility.

In some embodiments, the antibiotic susceptibility of a sample is used to determine and optionally administer a treatment course of action (e.g., choice of one or more antibiotics to administer to a subject).

In some embodiments, a computer-based analysis program is used to translate the raw data generated by the detection assay (e.g., the presence, absence, or amount of a given microorganism) into data of predictive value for a clinician. The clinician can access the predictive data using any suitable means. Thus, in some preferred embodiments, the present disclosure provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present disclosure contemplates any method capable of receiving, processing, and transmitting the information to and from laboratories conducting the assays, information providers, medical personal, and subjects. For example, in some embodiments of the present disclosure, a sample (e.g., a blood sample) is obtained from a subject and submitted to a profiling service (e.g., clinical lab at the medical facility, genomic profiling business, etc.) to generate raw data. Where the sample comprises a tissue or other biological sample, the subject may visit a medical center to have the sample obtained and sent to the profiling center, or subjects may collect the sample themselves (e.g., a blood sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (e.g., presence and/or antibiotic resistance status of bacteria in the sample), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of a microorganism or an antibiotic resistant microorganism) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action (e.g., choice of antibiotic).

In some embodiments, the present disclosure provides kits and systems for the isolation, and analysis of nucleic acids (e.g., microorganism specific nucleic acid). In some embodiments, kits include reagents necessary, sufficient or useful for detection of nucleic acids (e.g., primers, nanoparticles, metals, enzymes, buffers, controls, instructions, instruments, processing devices, etc.).

In some embodiments, kits comprise one or more containers that comprise primers, nanoparticles, metals, enzymes, buffers, controls, instructions, and the like. In some embodiments, each component of the kit is packaged in a separate container. In some embodiments, the containers are packed and/or shipped in the same kit or box for use together. In some embodiments, one or more components of the kit are shipped and/or packaged separately.

In some embodiments, systems include automated sample and reagent handling devices (e.g., robotics).

EXPERIMENTAL

The following examples are provided in order to demonstrate and further illustrate certain preferred embodiments and aspects of the present disclosure and are not to be construed as limiting the scope thereof.

Example 1

Direct Detection of Bacteria in Whole-Blood Via NR—PCR

Figure 3:
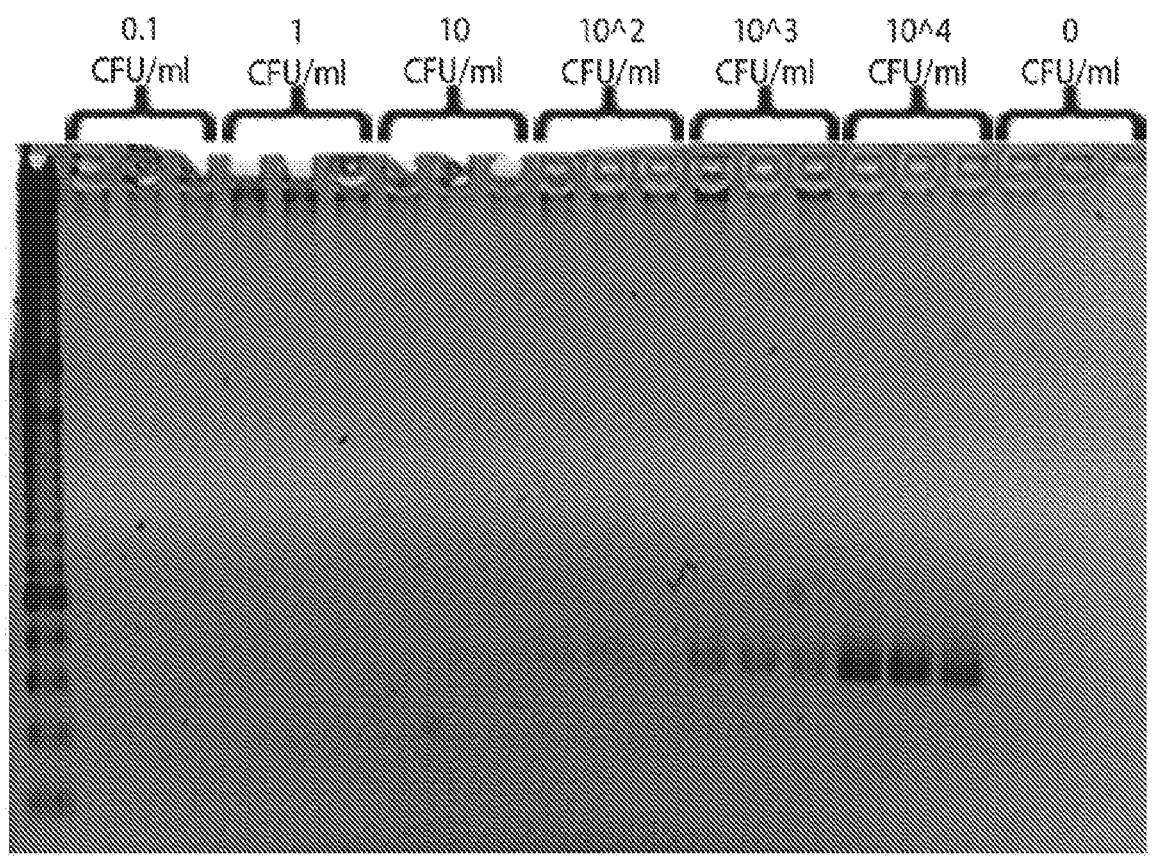
FIG. 3 shows gel-electrophoresis of mecA PCR on whole-blood spiked with serial dilutions of live MRSA ranging from 0-104 CFU/ml of blood.
Figure 4:
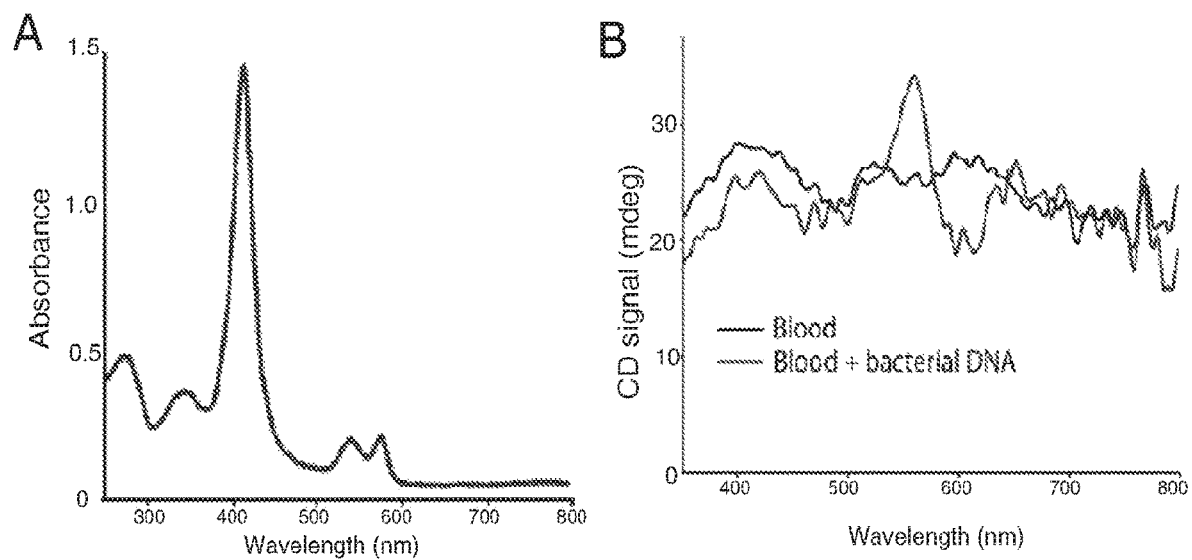
FIG. 4 shows (A) UV-vis spectra for whole-blood. (B) CD spectra for whole-blood with and without bacterial DNA blood spiked with serial dilutions of live MRSA ranging from 0-$10^4$ CFU/ml of blood.
Figure 5:
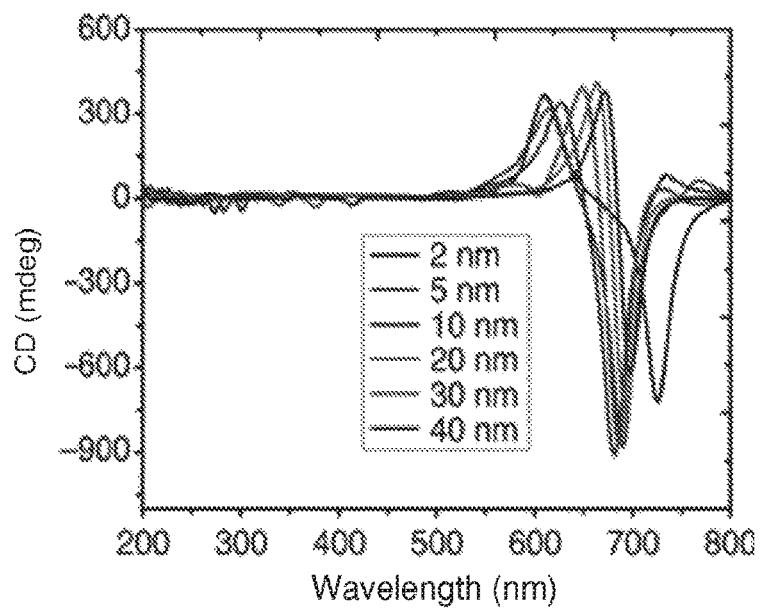
FIG. 5 shows calculated CD spectra for NR complexes with gaps of 2, 5, 10, 20, 30, and 40 nm.

Many components of whole-blood (e.g., hemoglobin) generate chiroplasmonic signals that can interfere with the CD spectral detection. Whole-blood is a complex medium containing whole cells, proteins/peptides, lipids, and many small molecules that can interfere with nucleic acid detection. There are several known inhibitors of PCR within whole-blood including hemoglobin and immunoglobulin as well as proteases (Kermekchiev, M. B., et al. Nucleic Acids Research, doi:10.1093/nar/gkn1055 (2009)). To combat this, a specific polymerase kit designed for whole-blood is used. Using this kit, it was possible to detect the presence of the methicillin resistance gene (mecA) in whole-blood spiked with live methicillin resistant *Staphylococcus aureus* (MRSA) at concentrations down to ~300 CFU/ml with simple gel electrophoresis (FIG. 3).

Whole-Blood NR—PCR Assay

Figure 2:
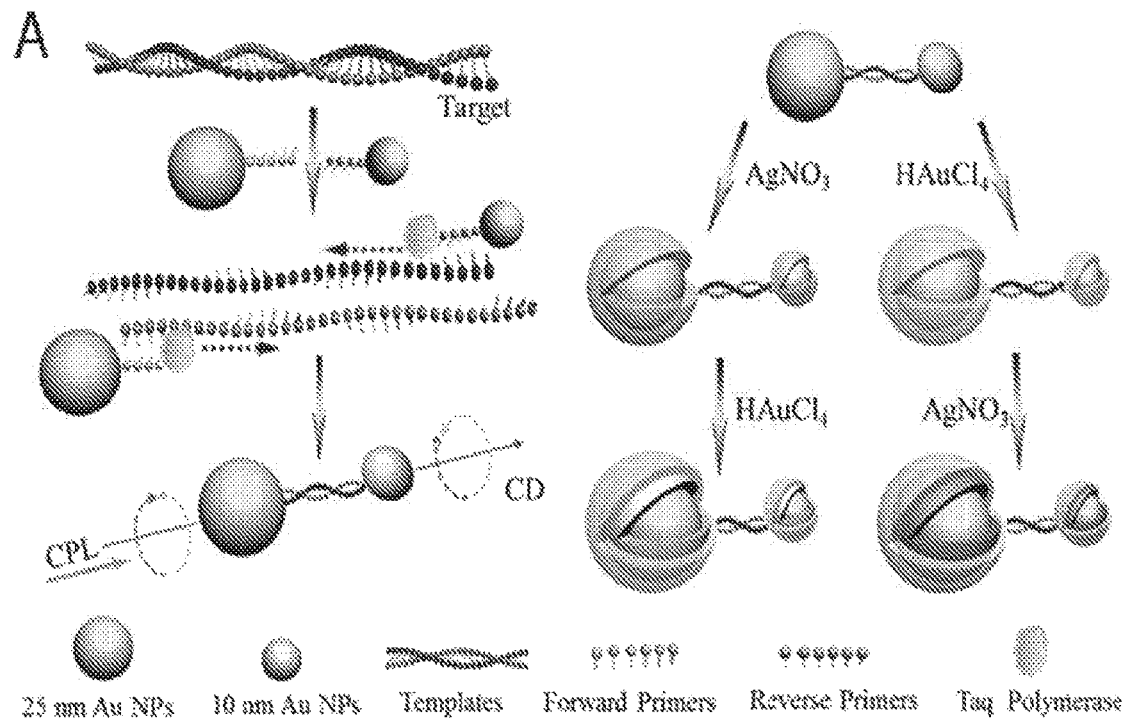
FIG. 2 shows (A) Illustration of PCR-assembled nanoparticle complexes and post-assembly deposition of Ag and Au shells. (B) Shell-mediated spectral modulation of chiroplasmonic bands. (C) Analytic calibration curve relating the intensity of CD bands with Au shell and the concentration of DNA.
Figure 2:
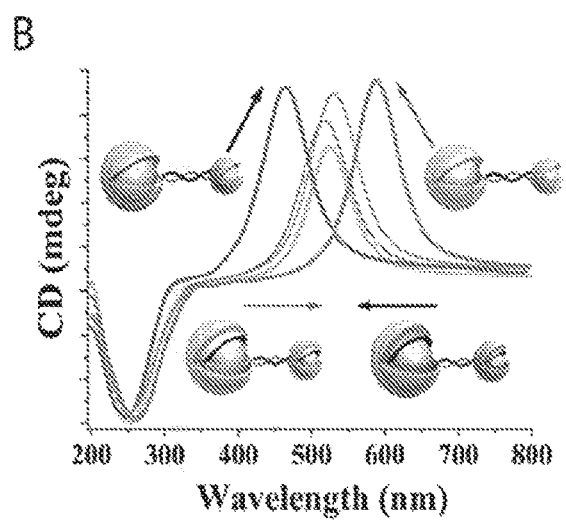
Figure 2:
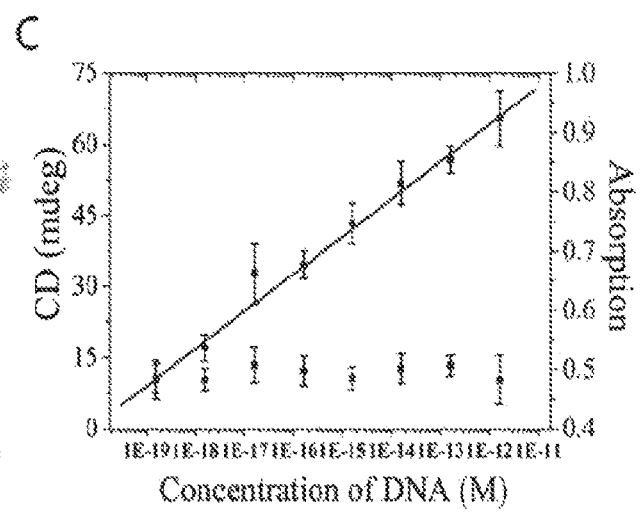

Data shows that post-PCR NR 'ladders' can be shell-coated to modulate the spectral CD bands (FIG. 2). Specifically, Ag shells generate a blue-shift in the peak CD band, while Au shells create a red shift. Copper shells, which generate a large red-shift, have also been tested. These spectral shifts also depend on the shell thickness 8. Shell thickness is controlled by the amount of metal added in the shell-coating reaction. This control of the CD spectral bands allows one to move the peaks to a less noisy part of the whole blood spectrum. It was found that additional reduction of the Cu and Au shells via increasing concentrations of $NH_2OH.HC$ adds additional control of the spectral peak positions and their intensity.

The peak CD signal intensity for NR—PCR reactions in whole blood is evaluated as a function of shell thickness for three metals, (i.e., Au, Ag, and Cu). Genomic DNA from *Staphylococcus aureus* COL is used as a template for the PCR reactions. This strain is a prototypical MRSA strain. Genomic DNA is isolated from mid-log phase cultures of *S. aureus* using lysostaphin (Sigma-Aldrich, St. Louis, Mo.), Trizol (Life Technologies, Carlsbad, Calif.) and a QIAamp DNA mini kit (Qiagen, Hilden, Germany). Au NR is synthesized by growth from Au seeds and modified for conjugation with PCR primers for *S. aureus* (Table 1) in an SBS configuration (FIG. 1C) as previously described (Ma et al., supra). PCR reactions are run using the 5× Phusion Blood Direct PCR kit (Thermo Fisher Scientific, Waltham, Mass.) with template genomic DNA and Au— NR conjugated primers. The thermal cycling protocol begins with a 5 min predenaturation step at 95° C., followed by 20 cycles of 95° C. denaturation (5 s), 50-65° C. annealing (5 s) and 72° C. extension (15-30 s) steps, followed by a further extension for 10 min at 72° C. Last, the PCR system will be held at 4° C. for 10 min. Shell coatings are applied based on a previously described protocol (Zhao et al., supra). Briefly, PCR products are centrifuged at 7000 rpm for 5 min, the precipitate will be re-suspended in PBS-CTAB (20 mM CTAB). Then, $AgNO_3$ (0.1 mM-10 mM) plus 0.1 M ascorbic acid; HAuCl4 (0.3-10 mM) plus 1 mM $NH_2OH.HCl$; or $CuCl_2$ (0.5-5 mM) plus 1 mM $NH_2OH.HCl$ are mixed into the PCR productions. After reacting for 5 min, the mixtures are centrifuged at 6000 rpm for 5 min. The precipitate is then dissolved in deionized water and UV-vis and CD spectra are obtained via JASCO J-815 spectrophotometer.

It is contemplated that a shift toward the near red portion of the spectrum provides the best signal-to-noise ratio and highest assay sensitivity.

Comparison with Standard Blood Culture

The sensitivity and specificity of the assay is confirmed by comparison with the current clinical gold-standard, namely blood culture.

Whole human blood obtained from healthy donors (commercially obtained from Valley Biomedical, Virginia) is spiked with defined concentrations of methicillin sensitive (MSSA) and resistant (MRSA) *S. aureus* and wild-type *Escherichia coli*. All bacterial strains are available as frozen glycerol stocks stored at −80° C. A single colony of a given species is inoculated in tryptic soy broth with 1% glucose (TSBG) and grown to mid-log. The bacterial are then be serially diluted in 10× increments. One aliquot of each dilution is used to spike a whole blood sample. The other is used for plating and colony counting. Blood known not to contain bacteria is used as negative control. The samples ae simultaneously processed for NR—PCR (see Table 1 for primer sequences) and for standard blood culture. Test samples are prepared by different laboratory staff than those running the platform assay. Plots of CD intensity vs bacterial concentration are used to determine the limit of detection. Standard 2×2 tables are constructed to determine the sensitivity and specificity.

If unprocessed blood is used, and single molecule detection is achieved, the maximum theoretic limit of detection is 50 CFU/ml. In some instances, initial denaturation is performed at 98° C. on 2 ml of whole blood followed by centrifugation to concentrate large macromolecules (including DNA) prior to NR—PCR. Multiple (~100) simultaneous NR—PCR reactions for the same sample akin to digital PCR but without the complexity of generating picoliter size reactions are also performed in some instances.

Example 2

CD Peak Wavelength and PCR Transcript Length

Given the need to not only detect but also ID specific bacterial species in the blood, in some embodiments, the NR—PCR assay provides a method for multiplex detection of the most common pathogens. Shell coatings can modulate the position of CD bands over a wide range of the visual spectrum. In addition, the structure of an individual NR complex provides narrow band modulation. Based on numeric simulation, the gap or distance between NRs, bridged by the DNA transcript, may also change the peak CD wavelength (FIG. 5), although over a much narrower range.

This provides a method for multiplexing. That is, multiple PCR reactions with different transcript lengths are run in the same tube and each unique product detected at different wavelengths.

The mecA gene is used as a test case. Table 2 shows primer sets for mecA with transcript lengths that vary from 99 to 402 bps. Whole-blood is spiked with genomic DNA isolated from MRSA. Using the optimized NR—PCR conditions determined above, CD spectra are generated for individual analytes with each of these primer sets. CD spectra are overlaid and the peak wavelength for each primer set is determined. This data are then used to generate a plot of CD peak vs transcript length. To evaluate the ability to perform multiplexed reactions, whole-blood is spiked with either MSSA or MRSA as described above. NR—PCR reactions that contain two NR-primer sets (one for mecA—99 bps; and one for femA—306 bps) each are run and CD spectra obtained. Spectral differences generated by two different NR complexes in the same tube are determined by comparing the spectra of the MRSA samples, which have two template reactions—mecA and femA, with the spectra of the MSSA samples which have one—femA only. Quantitative comparisons are made via principle component analysis.

TABLE 1

PCR primers

| Gene | Sequence | | SEQ ID NO: | Description |
|---|---|---|---|---|
| 16srRNA | Forward: | 5'-AGAGTTTGATCCTGGCTCAG-3' | 1 | This 16s target detects all Gram-positive, Gram-negative, and anaerobic bacteria[27] |
| | Reverse: | 5'-GTATTACCGCGGCTGCTGG-3' | 2 | |
| femA | Forward: | 5'-AACTGTTGGCCACTATGAGT-3' | 3 | The femA gene is unique to S. aureus[28] |
| | Reverse: | 5'-CCAGCATTACCTGTAATCTCG-3' | 4 | |
| mecA | Forward: | 5'-AAGCGACTTCACATCTATTAGGTTAT-3' | 5 | The mecA gene confers high level methicillin resistant to S. aureus[28] |
| | Reverse: | 5'-TATATTCTTCGTTACTCATGCCATAC-3' | 6 | |

TABLE 2 mecA primers

| Transcript Length | Sequence | | SEQ ID NO: |
|---|---|---|---|
| 99 | Forward: | 5'-CATTGATCGCAACGTTCAATTT-3' | 7 |
| | Reverse: | 5'-TGGTCTTTCTGCATTCCTGGA-3' | 8 |
| 204 | Forward: | 5'-CCACCCTCAAACAGGTGAAT-3' | 9 |
| | Reverse: | 5'-AACGTTGTAACCACCCCAAG-3' | 10 |
| 208 | Forward: | 5'-GCAGACAAATTGGGTGGTTT-3' | 11 |
| | Reverse: | 5'-CATCGTTACGGATTGCTTCA-3' | 12 |
| 402 | Forward: | 5'-AAGCGACTTCACATCTATTAGGTTAT-3' | 13 |
| | Reverse: | 5'-TATATTCTTCGTTACTCATGCCATAC-3' | 14 |

Example 3

Determination of Antibiotic Susceptibility

The ultra-sensitivity of NR—PCR allows detection of minute differences in bacterial concentration. NR—PCR reactions are run as a function of time for bacteria with and without the presence of antibiotics to determine the earliest time a difference is reliably detected. This establishes NR—PCR capacity for antibiotic sensitivity testing (AST).

Current clinical practice is to initiate broad-spectrum antibiotics for patients with suspected bacteremia and then narrow to target therapy once AST is performed. This one-size-fits-all approach is required because blood cultures with AST can take 72 hours or more. The general concept for AST is to evaluate the ability of a bacterium, detected in a clinical sample, to continue to grow or replicate in the presence of a specific antibiotic. If the bacterium is resistant to an antibiotic, it will replicate and its concentration will increase in the presence of that antibiotic. On the other hand, a susceptible bacterium will be unable to replicate in the presence of the antibiotic.

Figure 6:
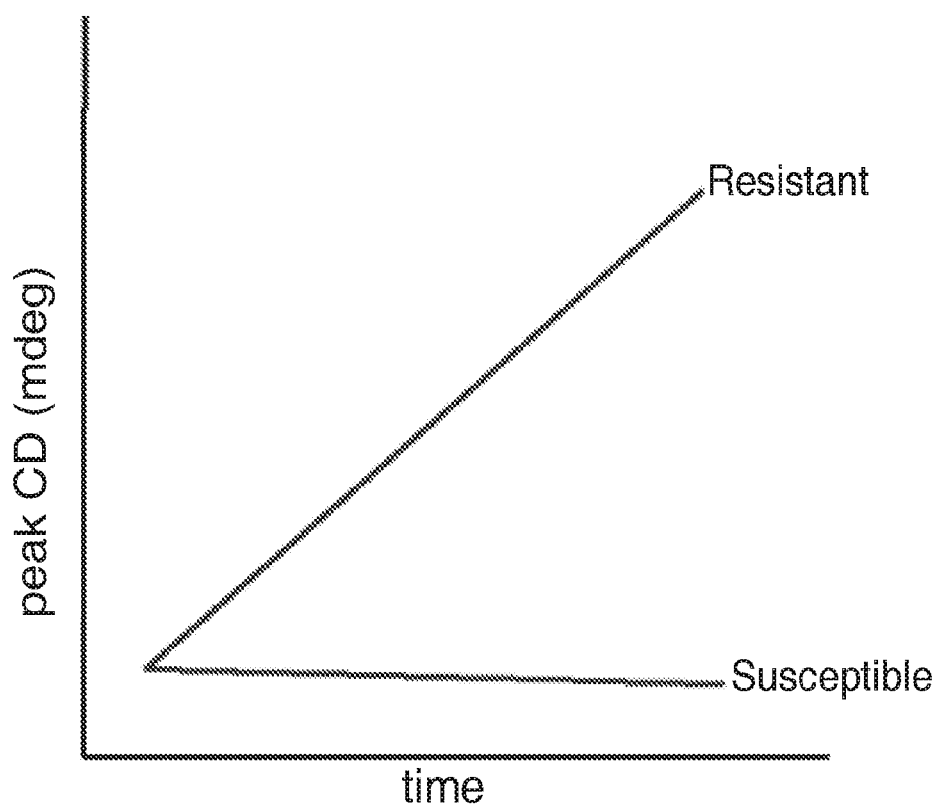
FIG. 6 shows hypothetical readout of AST from NR—PCR.

Given the high sensitivity of the NR—PCR system, detecting that difference in bacteria concentration is completed in a dramatically shorter period of time than traditional AST. For example, if a bacterium is detected at 10 CFU/ml, and in nutrient rich media it has a doubling time of 30 minutes, accounting for a typical lag phase prior to exponential growth, 2-3 doubling cycles are performed in 2 hours and a resulting increase in bacterial concentration up to 80 CFU/ml. The difference in the CD peak between 10 and 80 CFU/ml is discriminated using NR—PCR. Therefore, a bacterium that is resistant to antibiotic X will have an increase in the signal after a 2 hour incubation in media plus antibiotic X, while a different stain of the same species that is susceptible will have the same or decreased signal as indicated in FIG. 6.

To validate the NR—PCR assay's AST capabilities, two bacterial strains with different antibiotic susceptibility profiles are evaluated. Specifically, S. aureus SH1000 (methicillin-sensitive) is sensitive to amoxicillin and vancomycin while S. aureus COL (MRSA) is resistant to amoxicillin and sensitive to vancomycin.

The broth microdilution method (based on guidelines from Clinical and Laboratory Standards Institute) is used to determine the minimum inhibitory concentration (MIC) for amoxicillin and vancomycin with respect to both S. aureus strains. Briefly, a standard inoculum is incubated with varying concentrations of antibiotics in TSBG at 37° C. for 16 hours. The MIC is defined as the lowest concentration of antibiotic that inhibits bacterial growth. This concentration is used for the evaluation of AST with NR—PCR. Whole-blood is spiked with a known inoculum of each bacterial strain at a level just above the limit of detection determined above. An aliquot of that sample is immediately tested using the NR—PCR system to confirm detection and ID of the bacterial species. Then additional aliquots are inoculated into vials with TSBG supplemented with 1×MIC of amoxicillin or vancomycin. There is also be a media without antibiotic control to determine baseline growth. These vials are then incubated aerobically at 37° C. Samples are removed from each vial at 0.5, 1, 1.5, 2, and 3 hours and processed via NR—PCR to generate a CD peak versus time profile as shown in FIG. 6. The earliest time those growth curves can be statistically distinguished defines the minimum time required for AST.

We claim:

1. A method of detecting a plurality of microorganisms in a biological sample, comprising:
   a) performing nucleic acid amplification on a biological sample comprising whole blood that is not cultured or purified prior to performing said method using a plurality of forward and reverse primers, wherein said primers are attached to a gold nanoparticle to generate a plurality of amplification products of different lengths, wherein said amplification products are specific for a plurality of different microorganisms and wherein said amplification products assemble into side by side ladders comprising a gap distance between nanoparticles;
   b) depositing a metal shell on said nanoparticles to generate amplification products comprising metal coated nanoparticles; and
   c) detecting said amplification products comprising metal coated nanoparticles using circular dichroism (CD).

2. The method of claim 1, wherein said amplification is PCR.

3. The method of claim 1, wherein said forward and said reverse primers are attached to nanoparticles of different sizes.

4. The method of claim 1, wherein said nanoparticles are nanorods.

5. The method of claim 1, wherein said amplification products of different lengths exhibit CD peaks of different wavelengths.

6. The method of claim 1, wherein said metal shell is gold, copper, or silver.

7. The method of claim 1, wherein said microorganisms are bacteria.

8. The method of claim 7, wherein said bacteria are pathogenic bacteria.

9. The method of claim 7, wherein said bacteria are antibiotic resistant bacteria.

10. The method of claim 3, wherein said primers amplify a plurality of microorganism specific and/or antibiotic resistance genes.

11. The method of claim 1, wherein said method is performed in 3 hours or less.

12. The method of claim 1, wherein said method is performed in 2.5 hours or less.

13. The method of claim 1, further comprising the step of contacting said sample with an antibiotic prior to performing said method.

* * * * *